(12) United States Patent
Amino et al.

(10) Patent No.: US 7,612,214 B2
(45) Date of Patent: Nov. 3, 2009

US007612214B2

(54) ORGANIC AMINE SALTS OF GLUTAMIC ACID DERIVATIVES AND THEIR APPLICATION

(75) Inventors: Yusuke Amino, Kawasaki (JP); Kazuko Hirasawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 329 days.

(21) Appl. No.: 10/992,795

(22) Filed: Nov. 22, 2004

(65) Prior Publication Data

US 2005/0137246 A1 Jun. 23, 2005

(30) Foreign Application Priority Data

Nov. 21, 2003 (JP) ............................. 2003-391573

(51) Int. Cl.
*C07D 209/18* (2006.01)
(52) U.S. Cl. ..................................... 548/495
(58) Field of Classification Search ................. 548/495
See application file for complete search history.

(56) References Cited

U.S. PATENT DOCUMENTS

| 3,615,807 A | 10/1971 | Yates |
| 3,674,776 A | 7/1972 | Long et al. |
| 3,772,028 A | 11/1973 | Fico et al. |
| 3,954,816 A | 5/1976 | Bloom et al. |
| 4,066,676 A | 1/1978 | Bloom et al. |
| 4,975,298 A * | 12/1990 | Van Wyk et al. ............. 426/548 |
| 7,378,508 B2 * | 5/2008 | Chiu et al. .................... 536/7.1 |
| 2003/0228403 A1 | 12/2003 | Amino et al. |
| 2005/0118317 A1 * | 6/2005 | Amino et al. ................ 426/548 |

FOREIGN PATENT DOCUMENTS

| EP | 1 533 300 | 5/2005 |
| JP | 2003-171365 | 6/2003 |

OTHER PUBLICATIONS

Berge et al., 1977, Journal of Pharmaceutical Science, pp. 1-19.*
U.S. Appl. No. 11/627,700, filed Jan. 26, 2007, Amino, et al.
U.S. Appl. No. 11/505,997, filed Aug. 18, 2006, Mori, et al.

* cited by examiner

*Primary Examiner*—Rei-tsang Shiao
(74) *Attorney, Agent, or Firm*—Oblon, Spivak, McClelland, Maier & Neustadt, L.L.P.

(57) ABSTRACT

The present invention provides an organic amine salt of monatin, or crystal form thereof, and its application as well as a method for resolving the stereoisomers of monatin by forming its salt. The present invention further provides a salt form of monatin that is useful as a sweetening agent or as the active ingredient of a sweetener. The present invention also provides a method for preparing a salt of a particular stereoisomer of monatin with an organic amine by utilizing the difference of crystallinity or solubility of the salt of the stereoisomer of monatin with the organic amine. The present invention also relates to a use of the salt in a method for preparing a metal salt of monatin in which the organic amine is replaced by a metal such as sodium, potassium, or the like.

20 Claims, 2 Drawing Sheets

FIG. 1
Monatin (2R, 4R)·(R)-(−)-2-Phenylglycinol salt
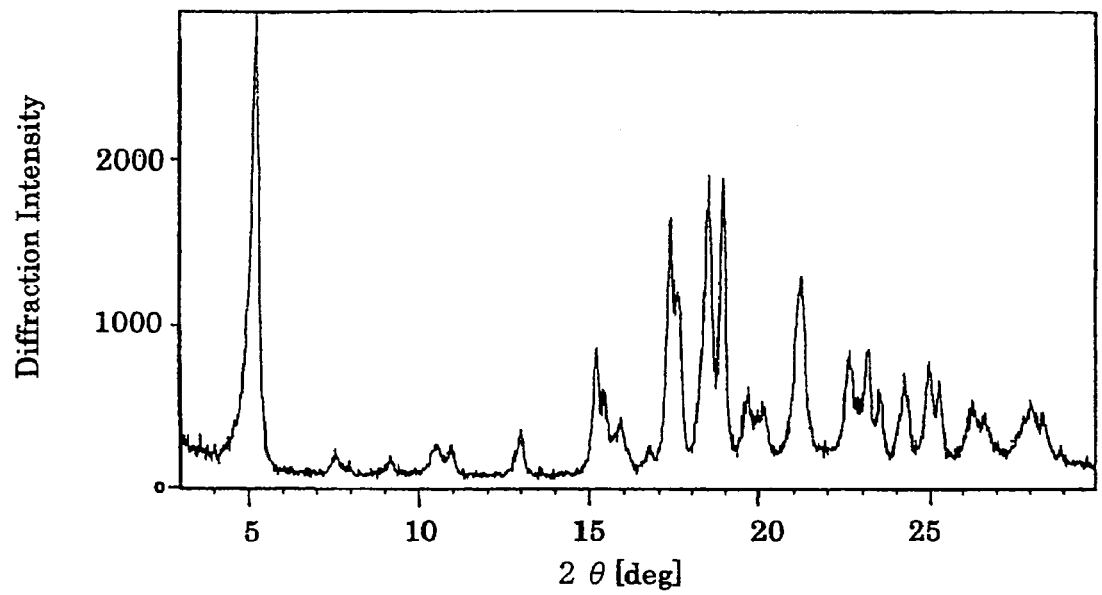
Monatin (2R, 4S)·(R)-(−)-2-Phenylglycinol salt
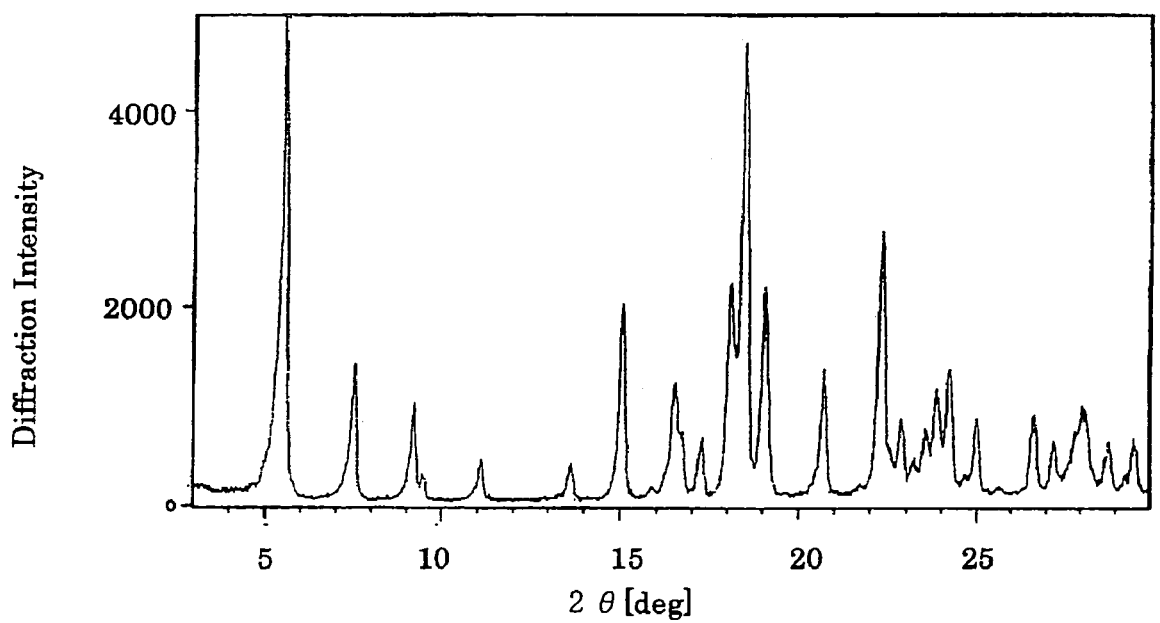
FIG.2

FIG. 3
Monatin (2R, 4R) · L-Valinol salt
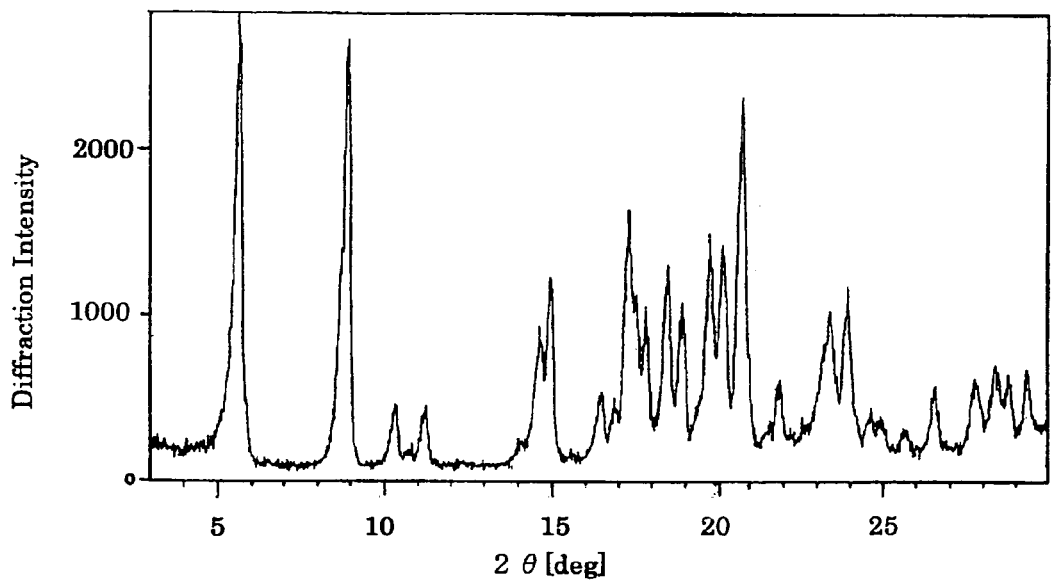
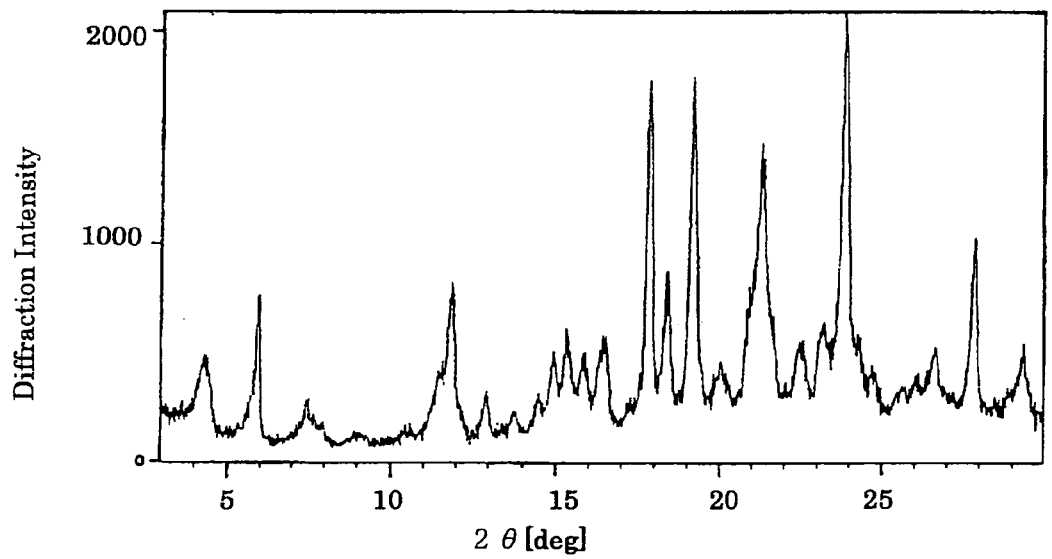
(2R, 4R)-Monatin/Aspartame crystal(salt)
FIG.4

ORGANIC AMINE SALTS OF GLUTAMIC ACID DERIVATIVES AND THEIR APPLICATION

CROSS-REFERENCE TO RELATED APPLICATIONS

The present application claims priority to Japanese Patent Application No. JP 2003-391573, filed on Nov. 21, 2003, the entire contents of which are incorporated herein by reference.

BACKGROUND OF THE INVENTION

1. Field of the Invention

The present invention provides an organic amine salt of monatin and its application as well as a method for resolving the stereoisomers of monatin by forming its salt. More particularly, the present invention relates to a salt form of monatin that is useful as a sweetening agent or as the active ingredient of a sweetener. Within the present invention the salt is formed with an alkylamine, aminoalcohol, amino acid, peptide ester, or the like. The present invention further provides a method for preparing a salt of a particular stereoisomer of monatin with an organic amine by utilizing the difference of crystallinity or solubility of the salt of the stereoisomer of monatin with the organic amine. The use of the salt involves a method for preparing a metal salt of monatin in which the organic amine is replaced by a metal such as sodium, potassium, or the like. The salt includes a single product or a mixture of two or more of the (2S,4S)-isomer, (2S,4R)-isomer, (2R,4R)-isomer and (2R,4S)-isomer of monatin.

2. Discussion of the Background

In recent years, there has been an increased incidence of problems resulting from excessive ingestion of sugar, for example obesity and various types of diseases accompanied thereby. Therefore, development of a low-calorie sweetening agent to serve as a sugar substitute is in high demand. In addition to strength of the sweetness, several additional characteristics and requirements should also be satisfied by the sugar-substitute including: low-calorie, high safety (i.e., little or no side effects), high stability against heat or acid, excellent sweetness quality, and low cost.

Currently, several types of sweetening agents have been used or proposed. For example, aspartame has gained notoriety as a widely used sweetening agent, due to its potent sweetness strength and quality as well as its ease for industrial manufacture on a large scale and its excellent safety. Furthermore, studies on aspartame derivatives have also been extensively conducted. In addition thereto, sweetening materials having various characteristics have been proposed as a sweetening agent and investigations toward the practical use thereof have been conducted. Additional sweetening agents that are currently used include naturally occurring thaumatin, glycyrrhizin, stevioside and the like which are derived from plants and can be collected on a large scale. However, there still exists a strong desire to develop a sweetening material that can be practically employed as a sweetening agent and has a high sweetening strength.

Monatin is a naturally occurring amino acid derivative isolated from root bark of *Schlerochiton ilicifolius* which is a self-sown plant in the Northwestern Transvaal region of South Africa, and R. Vleggaar et al. (J. Chem. Soc. Perkin Trans., 3095-3098, (1992)), reported its structure as being (2S,4S)-2-amino-4-carboxy-4-hydroxy-5-(3-indolyl)pentanoic acid ((2S,4S)-4-hydroxy-4-(3-indolylmethyl)-glutamic acid). Additionally, according to Vleggar et al. the degree of sweetness of the (2S,4S) isomer referred to as being derived from this natural plant has been reported to be 800 times, or maybe 1400 times of sucrose. There are some methods reported on the synthesis of monatin, but many Although some processes for the synthesis of monatin have been reported, a suitable industrial process has not been reported to date. Examples of synthesis of monatin can be found in South Africa (ZA) Patent Application No. 87/4288, C. W. Holzapfel et al., Synthetic Communications, 24 (22), 3197-3211 (1994), U.S. Pat. No. 5,994,559, and K, Nakamura et al., Organic Letters, 2, 2967-2970 (2000). Therefore, a derivative having a sweetness strength equivalent to or greater than that of monatin, which can be more readily produced than monatin, is desired and would have more feasible practicability as a sweetening agent.

In order to isolate various stereoisomers of monatin to a high purity, a method of crystallization is first conceivable. In this connection, the following methods account for the state of the known art regarding the crystallization of monatin (including the free moatin, salt, and so on).

In R. Vleggaar et al., J. Chem. Soc., Perkin Trans., 3095-3098 (1992), the authors disclose the preparation of the free monantin ((2S,4S) isomer) crystals from a mixture of water, acetic acid and ethanol (1:1:5) and disclose the melting point to be 216-220° C. South Africa Patent Application. No. 87/4288 (P. J. van Wyk et al., ZA 87/4288) disclose the melting point of the free monatin ((2S,4S) isomer) (crystalline solid) to be 247-265° C. (decomposition), though its salts are amorphous solids. Holzapfel et al., Synthetic Communications, 24(22), 3197-3211 (1994), disclose the crystals of a mixture of the synthetic (2S,4S) and (2R,4R) free monatin isomers crystallized twice from a mixture of water and acetic acid (10:1), of which the melting point is 212-214° C.

Accordingly, only the (2S,4S)-isomer and a mixture of the (2S,4S)- and (2R,4R)-isomers of monatin are known as monatin crystals. Moreover, although the existence of the ammonium salt, alkali metal salt and alkaline earth metal is suggested as salts, these salts have never been isolated as crystals and hence never applied to resolution of the optical isomers. In other words, merely a method of utilizing the crystals of free monatin is known as the only method for isolation and purification of crystalline monatin, and the existence of the ammonium salt and a variety of metal salts has merely been suggested as monatin salt. On the other hand, no salt of monatin with an organic amine has been known at all and it is not clear whether such a salt can be prepared or not. Therefore, there is no attempt to make the crystal of the organic amine salt of monatin in order to separate the stereoisomer of monatin or utilize it as a sweetening agent. Accordingly, there now exists a requirement for the development of a method of preparing a salt of monatin with an organic amine and further crystalize the salt, and to develop a method for resolution of the respective stereoisomers of monatin by utilizing the salt or examine the use of monatin as a sweetening agent on a viewpoint of practical use.

SUMMARY OF THE INVENTION

It is an object of the present invention to provide novel organic amine salts of monatin and crystals thereof.

It is also an object of the present invention to provide a sweetening agent containing the organic amine salts of monatin and crystals thereof.

It is yet another object of the present invention to establish a method for resolving the respective stereoisomers of monatin utilizing the difference of their crystallinity or solubility.

Further it is an object of the present invention to elucidate the usefulness of the organic amine salts as sweetening agents and to provide a convenient method for converting the resulting organic amine salt of monatin into another salt with another base, for example, a salt with sodium or potassium.

Though the conformation of the natural type of monatin has been reported to be a (2S,4S)-isomer as mentioned above, in the present invention, all of the compounds having the same chemical structure are named generically as "monatin", and the respective stereoisomers are accordingly called as "(2S,4R)-isomer of monatin", "(2R,4S)-isomer of monatin", or "(2R,4R)-isomer of monatin". These stereoisomers including (2S,4S)-isomer of monatin are designated as "the 4 types of stereoisomers".

In addition to the alkylamine, the organic amine includes compounds having an amino group, such as aminoalcohols, amino acids, peptide esters, etc.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 1 shows a powder X-ray diffractometry chart of the crystals of (2R,4R)-monatin/(R)-(−)-2-phenylglycinol salt after drying in Example 1.

FIG. 2 shows a powder X-ray diffractometry chart of the crystals of (2R,4S)-monatin/(R)-(−)-2-phenylglycinol salt after drying in Example 6.

FIG. 3 shows a powder X-ray diffractometry chart of the crystals of (2R,4R)-monatin/L-valinol salt after drying in Example 14.

FIG. 4 shows a powder X-ray diffractometry chart of the (2R,4R)-monatin/aspartame mixed crystal (salt) after drying in Example 22.

DETAILED DESCRIPTION OF THE INVENTION

Unless specifically defined, all technical and scientific terms used herein have the same meaning as commonly understood by a skilled artisan in chemistry and food sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In order to solve the above-mentioned problems, the present inventors worked assiduously to elucidate the salts of monatin with organic amines. A mixture of the stereoisomers of monatin synthesized by a conventional synthetic method was prepared and optically resolved.

Thus in an embodiment of the present invention is a method for preparing the salts in crystal forms from each stereoisomer of the optically resolved monatin. Further, a variety of organic amines were developed and their physical properties were examined.

Several conditions for crystallization (deposition of crystals) were explored relative to a mixture of the stereoisomers of monatin and a variety of combinations of the respective stereoisomers and optically active organic amines or inactive organic amines. These conditions included the kind of solvent, concentration of the substrate, temperature, pH, a co-existing base, etc. As a result, it was determined that diversely combined stereoisomers of monatin can be crystallized, per se, as organic amine salts, resulting in a method for resolving the respective stereoisomers of monatin. In this connection, a method for converting these salts into free monatin or a variety of metal salts, which can be used practically as a sweetening agent, has also been proffered by the present invention. In particular, it becomes possible to resolve the enantiomer of monatin by using an optically active organic amine as a base, though it was difficult in a conventional crystallization. This method of resolution is excellent in this aspect.

Further, it has also been determined that the crystals of the salt of monatin with an edible organic amine (amino acid, dipeptide ester, etc.) can be used to provide a sweetening agent or food and drink.

The invention was completed, in part, based on the above-mentioned various findings.

Thus, the present invention involves (1) novel salts of monatin with organic amines; (2) a novel method for resolution of the stereoisomers of monatin utilizing crystals of the novel salts of monatin with organic amines; (3) a method for conversion of the salts of monatin with organic amines into metal salts or other salts; and (4) the use of the novel salts of monatin with organic amines as sweetening agents.

As used herein, said crystals of the salts may be in forms of hydrates or solvates.

There is no particular limitation imposed on the form of the salts of the present invention. When the salts are intended to be used in food as the final product, naturally they may be employed as salts that are suitable for use in food (i.e., suitable for animal consumption). In addition, the salts that are suitable for isolation, purification, or resolution (in the form of crystals) are also valuable.

A conventional or well-known method for salt formation can be utilized according to the illustration (Examples, etc.) of the present invention to yield the desired salts.

The crystals of the invention include the following contents [1] to [21].

In this connection, the natural type monatin, (2S,4S)-isomer, as well as the unnatural monatin, (2S,4R)-, (2R,4R)- and (2R,4S)-isomers are represented by the following structural formulae (3), (4), (5) and (6).

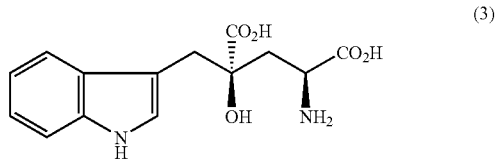
(3)

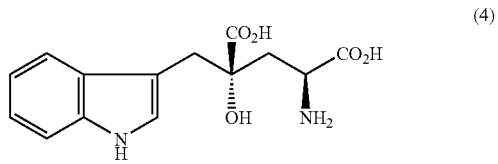
(4)

-continued

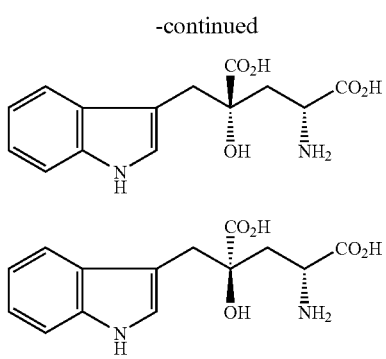

[1]

As for the salt of monatin stereoisomer, the salts of (2S,4S)-, (2S,4R)-, (2R,4R)- and (2R,4S)-isomers and a mixture of at least two of the isomeric salts are exemplified. The crystals of these salts may be in the forms of hydrates or solvates.

Among these stereoisomeric salts, those of the (2R,4S)- and (2R,4R)-isomers are more preferred, and further those of the (2R,4R)-isomer are most preferred. The crystals of these salts involved in the invention are preferred in view of the relative ease in isolation and purification.

[2]

The above-mentioned crystals of the salts of unnatural stereoisomers of the invention may preferably contain the salts (including the form of hydrate and solvate) of the isomers in the chemical purity of at least about 95%, and more preferably in at least about 97%.

[3]

In addition, the above-mentioned crystals of the salts of unnatural stereoisomers of the invention may preferably have the optical purity of at least about 90%, more preferably at least about 94%, and even more preferably at least about 98%. For example, the highly optically pure product of the salt of (2R,4R)-isomer of monatin (including hydrate, solvate, or a mixture of these salts) can be exemplified.

[4]

As the organic amine used to form the salt of monatin as in the present invention, organic amines represented by the following general formula (1) can be exemplified.

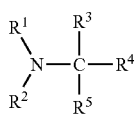

In the formula (1), $R^1$ and $R^2$ each represents a substituent selected from hydrogen atom, alkyl groups of 1 to 10 carbon atoms, and aralkyl groups of 1 to 12 carbons;

$R^3$, $R^4$ and $R^5$ each represents a substituent selected from hydrogen atom, alkyl groups of 1 to 10 carbon atoms, arylalkyl groups of 1 to 12 carbon atoms, alkoxyalkyl groups of 1 to 10 carbon atoms, hydroxyalkyl groups of 1 to 10 carbon atoms, aminoalkyl groups of 1 to 10 carbon atoms, carboxyl group, alkoxycarbonyl groups of 1 to 10 carbon atoms, carboxyalkyl groups of 1 to 10 carbon atoms, alkoxycarbonylalkyl groups of 1 to 10 carbon atoms and guanidinoalkyl groups of 1 to 10 carbon atoms; wherein the aryl group of the arylalkyl group includes heterocycles or benzene rings which have an optional number of hydroxyl group, alkoxy group of 1 to 3 carbon atoms and alkyl group of 1 to 3 carbon atoms as (a) substituent(s);

or optional two or more substituents in $R^1$ to $R^2$ may form a cyclic structure through an alkylene group (methylene group, ethylene group, etc.), heteroatom (nitrogen atom, oxygen atom, etc.) or aromatic substituent;

when the carbon atom represented by "C" in the formula (1) is an asymmetric carbon, its configuration may be any of R, S or RS.

[5]

As the organic amine used in formation of the salt of monatin in the invention, compounds represented by the following general formula (2) can be exemplified.

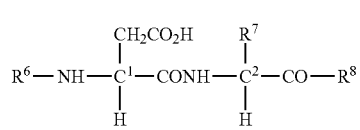

In the above formula (2), $R^6$ represents a substituent selected from alkyl groups and arylalkyl groups of 1 to 12 carbon atoms; wherein the aryl group of the arylalkyl group includes heterocycles or benzene rings which as (a) substituent(s) have an optional number of hydroxyl group, alkoxy group of 1 to 3 carbon atoms and alkyl group of 1 to 3 carbon atoms;

$R^7$ represents a substituent selected from alkyl groups of 1 to 4 carbon atoms, hydroxymethyl group, 2-hydroxyethyl group, phenyl group, p-hydroxyphenyl group, 2-furyl group, benzyl group, p-hydroxybenzyl group, cyclohexylmethyl group and t-butylthiomethyl group;

$R^8$ represents a substituent selected from alkoxy groups of 1 to 3 carbon atoms, alkylamino groups of 1 to 15 carbon atoms, cycloalkylamino groups of 1 to 15 carbon atoms and arylalkylamino groups of 1 to 12 carbon atoms; wherein the alkylamino and cycloalkylamino groups may contain an ether linkage or thioether linkage and may have a hydroxyl group as a substituent; and the aryl group of the arylalkylamino group includes heterocycles or benzene rings which have an optional number of hydroxyl group, alkoxy group of 1 to 3 carbon atoms or alkyl group of 1 to 3 carbon atoms as (a) substituent(s);

the configuration of the carbon atoms represented by "$C^1$" and "$C^2$" in the above formula (2) may be any of R, S or RS.

[6]

The above-mentioned organic amine used in formation of the salt of monatin of the invention includes compounds selected from alkylamines, alkyldiamines, alkaloids, aminoalcohols, amino acids, amino acid esters, amino acid amides, peptides, peptide esters and peptide amides.

[7]

The above-mentioned organic amine used in formation of the salt of monatin of the invention includes compounds selected from alkylamines such as benzylamine, cyclohexylamine, dicyclohexylamine, neopentylamine, α-phenylethylamine, α-phenylporpylamine and α-methoxymethylbenzylamine, alkaloids such as quinine, quinidine, cinchonine, cinchonidine and brucine, aminoalcohols such as alaninol, phenylglycinol, leucinol, isoleucinol, t-leucinol, valinol, phenylalaninol and ephedrine, amino acids such as lysine, ornithine and arginine, amino acid amides such as alanine amide, valine amide and phenylglycine amide, amino acid esters such as alanine methyl ester and valine ethyl ester, and peptide esters or peptide amides such as aspartame, neotame and alitame.

[8]
An embodiment of the present invention relates to a method for resolution of the stereoisomers of monatin. The embodiment more specifically relates to a method for resolving the stereoisomers of monatin which comprises mixing a mixture containing at least two stereoisomers of monatin with a particular organic amine in a particular solvent and recovering selectively the generated organic amine salt of a particular steroisomer of monatin utilizing the easiness of generation of the crystalline organic amine salt with the particular steroisomer of monatin or the difference of their solubility.

[9]
An alternate embodiment of the present invention relates to another method for resolution of the stereoisomers of monatin. This embodiment more specifically relates to a method for resolving the stereoisomers of monatin which comprises mixing a mixture of at least two optional species of monatin stereoisomers with an optically active organic amine of the particular organic amine in a particular solvent to yield a diastereoisomer salt, and recovering selectively the salt of the particular monatin stereoisomer with the organic amine utilizing the easiness of generation of their crystals or the difference of their solubility (a diastereomer method), is exemplified.

[10]
Yet another embodiment of the present invention relates to another method for resolution of the stereoisomers of monatin. This embodiment more specifically relates to a method for resolving the stereoisomers of monatin which comprises mixing a mixture of at least two optional species of monatin stereoisomers with an optically inactive organic amine of the particular organic amine in a particular solvent to yield a salt, and recovering selectively the salt of the particular monatin stereoisomer with the organic amine utilizing the easiness of generation of their crystals or the difference of their solubility (a preferential crystallization method), is exemplified.

[11]
As the above-mentioned organic amine used in resolution of the stereoisomers of monatin in the present invention, compounds represented by the following general formula (1) can be exemplified.

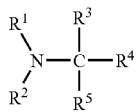

In the above formula (1),
$R^1$ and $R^2$ each represents a substituent selected from hydrogen atom, alkyl groups of 1 to 10 carbon atoms, and aralkyl groups of 1 to 12 carbons;
$R^3$, $R^4$ and $R^5$ each represents a substituent selected from hydrogen atom, alkyl groups of 1 to 10 carbon atoms, arylalkyl groups of 1 to 12 carbon atoms, alkoxyalkyl groups of 1 to 10 carbon atoms, hydroxyalkyl groups of 1 to 10 carbon atoms, aminoalkyl groups of 1 to 10 carbon atoms, carboxyl group, alkoxycarbonyl groups of 1 to 10 carbon atoms, carboxyalkyl groups of 1 to 10 carbon atoms, alkoxycarbonylalkyl groups of 1 to 10 carbon atoms and guanidinoalkyl groups of 1 to 10 carbon atoms; wherein the aryl group of the arylalkyl group includes heterocycles or benzene rings which have an optional number of hydroxyl group, alkoxy group of 1 to 3 carbon atoms and alkyl group of 1 to 3 carbon atoms as (a) substituent(s);

or optional two or more substituents in $R^1$ to $R^2$ may form a cyclic structure through an alkylene group (methylene group, ethylene group, etc.), heteroatom (nitrogen atom, oxygen atom, etc.) or aromatic substituent;

when the carbon atom represented by "C" in the formula (1) is an asymmetric carbon, its configuration may be any of R, S or RS.

[12]
As the above-mentioned organic amine used in resolution of the stereoisomers of monatin in the invention, organic amines represented by the following general formula (2) can be exemplified.

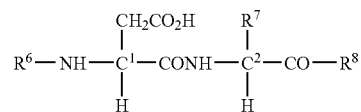

In the above formula (2),
$R^6$ represents a substituent selected from alkyl groups and arylalkyl groups of 1 to 12 carbon atoms; wherein the aryl group of the arylalkyl group includes heterocycles or benzene rings which as (a) substituent(s) have an optional number of hydroxyl group, alkoxy group of 1 to 3 carbon atoms and alkyl group of 1 to 3 carbon atoms;

$R^7$ represents a substituent selected from alkyl groups of 1 to 4 carbon atoms, hydroxymethyl group, 2-hydroxyethyl group, phenyl group, p-hydroxyphenyl group, 2-furyl group, benzyl group, p-hydroxybenzyl group, cyclohexylmethyl group and t-butylthiomethyl group;

$R^8$ represents a substituent selected from alkoxy groups of 1 to 3 carbon atoms, alkylamino groups of 1 to 15 carbon atoms, cycloalkylamino groups of 1 to 15 carbon atoms and arylalkylamino groups of 1 to 12 carbon atoms; wherein the alkylamino and cycloalkylamino groups may contain an ether linkage or thioether linkage and may have a hydroxyl group as a substituent; and the aryl group of the arylalkylamino group includes heterocycles or benzene rings which have an optional number of hydroxyl group, alkoxy group of 1 to 3 carbon atoms and alkyl group of 1 to 3 carbon atoms as (a) substituent(s);

the configuration of the carbon atoms represented by "$C^1$" and "$C^2$" in the above formula (2) may be any of R, S or RS.

[13]
The above-mentioned solvent used in resolution of the stereoisomers of monatin in the invention includes those selected from water, alcohols such as methanol, ethanol, isopropanol, and the like, tetrahydrofuran, acetonitrile or dimethylformamide (DMF), or mixtures thereof.

[14]
The above-mentioned organic amine used in resolution of the stereoisomers of monatin in the invention includes compounds selected from alkylamines, alkyldiamines, alkaloids, aminoalcohols, amino acids, amino acid esters, amino acid amides, peptides, peptide esters and peptide amides.

[15]

The above-mentioned organic amine used in resolution of the stereoisomers of monatin in the invention includes compounds selected from alkylamines such as benzylamine, cyclohexylamine, dicyclohexylamine, neopentylamine, α-phenylethylamine, α-phenylporpylamine and α-methoxymethylbenzylamine, alkaloids such as quinine, quinidine, cinchonine, cinchonidine and brucine, aminoalcohols such as alaninol, phenylglycinol, leucinol, isoleucinol, t-leucinol, valinol, phenylalaninol and ephedrine, amino acids such as lysine, omithine and arginine, amino acid amides such as alanine amide, valine amide and phenylglycine amide, amino acid esters such as alanine methyl ester and valine ethyl ester, and peptide esters or peptide amides such as aspartame, neotame and alitame.

[16]

In another embodiment of the present invention is a method for converting an organic amine salt of monatin into the corresponding metal salt with an alkali metal or alkaline earth metal of monatin. More specifically this embodiment relates to a method that comprises adding a corresponding alkaline solution to a solution of the organic amine salt of monatin for salt exchange to yield the corresponding metal salt of monatin as crystals.

The alkali metal salts involved in the conversion includes potassium salt, sodium salt, lithium salt, calcium salt, magnesium salt, and the like.

The solvent used in the salt exchange includes water, alcohols such as methanol, ethanol, isopropanol, and the like, tetrahydrofuran, acetonitrile and dimethylformamide (DMF), or mixtures thereof.

[17]

In another embodiment of the present invention is a method for converting an organic amine salt of monatin into a free monatin or metal salt. More specifically, the present invention relates to a method which comprises adding a corresponding alkaline solution to a solution of the organic amine salt of monatin to make it basic, and then removing the organic amine by extraction with an organic solvent or by adsorption on a strongly acidic ion exchange resin, followed by isolation of the free monatin or its metal salt as crystals, is exemplified.

The solvent used in conversion into the free state or used in the salt exchange includes water, alcohols such as methanol, ethanol, isopropanol, and the like, tetrahydrofuran, acetonitrile and dimethylformamide (DMF), or mixtures thereof.

The solvent used in extraction of the organic amine includes ethyl acetate, isopropyl acetate, ether, toluene, isopropanol, dichloromethane and chloroform, or mixtures thereof.

[18]

In another embodiment of the invention, a sweetening agent which contains a salt of monatin of the invention (including the above items [1] to [7]) is provided.

[19]

When the above-mentioned salt of monatin is used as a sweetening agent, the molar ratio of monatin and an organic amine is not necessarily theoretically equivalent, and either of monatin or the organic amine may be present in excess.

[20]

The sweetening agent may also contain carrier(s) and/or bulking agent(s) used in sweetener; for example, a so far known or utilized carrier and/or bulking agent may be used.

[21]

In addition, a carrier or filler that is known or will be developed for use in sweetening agents may be contained. Moreover, it is natural that the agent may contain (an) additive(s) that can be used in sweetening agents. The sweetening agent is used for animals, for example, in mammalian, particularly in human.

[22]

In another embodiment of the invention, a food and drink product to which sweetness is imparted by containing a salt of monatin of the invention (including the above items [1] to [7]) is provided.

[23]

The sweetening agent can be used as a part of a sweetener to be added to animal products, particularly food and drink products for human, for example, confectionaries, chewing gum, etc., in which sweetness is required. In addition, they may be added to a product such as toothpaste or chemicals in which a sweetener is used for keeping sanitary condition in the mouth or to orally given chemicals that require sweetness. The salts of monatin of the present invention can be used in formulation of the products, which contain a monatin salt of the invention to exhibit sweetness, or in a method of imparting sweetness to a product in need of being sweetened. They may be used according to a conventional method or well-known method for using sweeteners.

[24]

The above-mentioned sweetening agents and food and drink products may also contain other sweetening ingredients (sweeteners), particularly, at least one of sugars and artificial or natural sweeteners. For example, sucrose, acesulfame, sucralose, saccharin, stevioside, xylose, trehalose, sorbitol, maltitol, and the like may be used together.

Advantage of the Invention

According to the present invention, the salts of monatin with organic amine ingredients such as amino acids, aminoalcohols, dipeptide esters, etc., are provided as novel salts of a novel sweetening material monatin. The salts with amino acids or dipeptide esters can be used as sweetening materials. The salts and their crystals may be used as sweetening agents or their ingredients or as sweetening additives to food and drink products since they are stable and have high sweetness.

In addition, the present invention provides a method for making a salt of a mixture of monatin stereoisomers with an organic amine and obtaining the monatin stereoisomer utilizing the difference of their crystallinity or solubility. Providing a method for obtaining respectively highly pure stereoisomers of monatin, it becomes possible to provide sweetening agents with monatin and food and drink products to which sweetness is given.

Thus, the invention is industrially valuable, particularly in the field of food products.

Further, monatin in which its stereoisomers exist in diverse combinations can be crystallized as an organic amine salt, which can be resolved into the respective stereoisomers. The salt can be converted into the free isomer or a variety of metal salts valuable as practical sweetening agents. In particular, it becomes possible to resolve the enantiomer of monatin by using an optically active organic amine as a base, though it is difficult in a conventional operation for crystallization. In addition, monatin can be converted into the salts with edible organic amines (amino acids, dipeptide esters, etc.), which salts can be crystallized and blended with sweetening agents or food and drink products.

In the present invention, it is to be understood that the content of the active ingredient (i.e., the organic amine salt of monatin or crystal form thereof) in the sweetening agent/composition, as well as foods or beverages containing the same, can be adjusted as taste and texture dictate. However, in an embodiment of the present invention the concentration of the organic amine salt of monatin or crystal form thereof ranges from 0.0008 to 0.04% by weight, preferably from 0.004 to 0.012% by weight.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Materials and Methods

The mixture of monatin stereoisomers used in the invention can be synthesized according to the method as described in International Patent Application No. 2003059865 A1 (S. Kawahara et al., WO2003059865 A1), and separation of the respective isomers from the mixture can be achieved according to the method as described in International Patent Application No. 2003059865 A1 (S. Kawahara et al., WO2003059865 A1) or International Patent Application No. 2003045914A1 (Y. Amino et al., WO2003045914A1), though the synthetic or resolution method for monatin including a variety of stereoisomers is not limited to these methods.

$^1$H-NMR spectra were acquired with a Bruker AVANCE400 (400 MHz), and MS spectra were acquired with a Thermo Quest TSQ700. Optical rotation was determined by means of Jasco DPI-1000 (JASCO Corporation). As a positive ion-exchange resin, AMBERLITE IR120B H AG was used. Powder X-ray diffractometry was made with PW3050 (Phillips). The melting point was determined by employing a Micro Melting Point Apparatus (Yanaco).

Analysis of the salts by high performance liquid chromatography was made according to the following conditions.

(Analytical Condition 1)
Column: Inertsil ODS-80A 6×150 mm
Eluent: 12% $CH_3CN$ aq. 0.05% TFA
Flow rate: 1.5 ml/min
Detection: UV 210 nm
Column temperature: room temperature
(Analytical Condition 2)
Column: CROWNPAK CR (+)4×150 mm
Eluent: $HClO_4$ aq. (pH 2.0)/MeOH=90/10
Flow rate: 1.2 ml/min
Detection: UV 210 nm
Column temperature: room temperature Example 1

Optical Resolution of the (2R,4R)-isomer and (2S, 4S)-isomer of Monatin and Preparation of (2R,4R)-monatin/R-(−)-2-phenylglycinol Salt (Run 1)

A 1:1 mixture of (2R,4R)- and (2S,4S)-isomers of monatin ammonium salt (3.00 g; 9.52 mmole) and 0.656 g (4.76 mmole) of (R)-(−)-2-phenylglycinol were dissolved in 100 ml of 2.5% ammonia water, and the mixture was concentrated under reduced pressure to 10 ml. The resulting solution was stirred at room temperature to precipitate crystals, which were collected by filtration and washed with 10 ml of water. The resulting crystals were dissolved in 200 ml of water, and the solution was concentrated under reduced pressure to 10 ml. The crystals precipitated at room temperature were collected by filtration resulting in 0.994 g of (2R,4R)-monatin/(R)-(−)-2-phenylglycinol salt (2.31 mmole, optical purity 99.9%) in 48.5% yield (to (2R,4R)-monatin).

NMR (400 MHz, $D_2O$) δ: 1.76-1.83 (m, 1H), 2.42-2.46 (m, 1H), 2.97-3.01 (m, 1H), 3.16-3.20 (m, 1H), 3.36-3.39 (m, 1H), 3.57-3.67 (m, 2H), 3.89-3.93 (m, 1H), 7.05-7.09 (m, 1H), 7.12-7.16 (m, 2H), 7.28-7.42 (m, 6H), 7.64-7.66 (m, 1H). M.p. 161.1-177.8° C.

Example 2

Optical Resolution of the (2R,4R)-isomer and (2S, 4S)-isomer of Monatin and Preparation of (2R,4R)-monatin/R-(−)-2-phenylglycinol Salt (Run 2)

A 1:1 mixture of (2R,4R)- and (2S,4S)-isomers of monatin ammonium salt (300 mg; 0.970 mmole), 66.5 mg (0.485 mmole) of (R)-(−)-2-phenylglycinol and 0.24 ml (0.485 mmole) of 2N sodium hydroxide aqueous solution were dissolved in 30 ml of water, and the mixture was concentrated under reduced pressure to 3 ml. The resulting solution was stirred at room temperature to precipitate crystals. After standing at room temperature overnight, the crystals were collected by filtration and washed with 3 ml of water resulting in 132 mg of (2R,4R)-monatin/(R)-(−)-2-phenylglycinol salt (0.306 mmole, optical purity 99.9%) in 63.1% yield (to (2R, 4R)-monatin).

Example 3

Optical Resolution of the (2R,4R)-isomer and (2S, 4S)-isomer of Monatin and Preparation of (2R,4R)-monatin/R-(−)-2-phenylglycinol Salt (Run 3)

A 1:1 mixture of (2R,4R)- and (2S,4S)-isomers of monatin ammonium salt (300 mg; 0.970 mmole) and 133 mg (0.970 mmole) of (R)-(−)-2-phenylglycinol were dissolved in 30 ml of water, and the mixture was concentrated under reduced pressure to 3 ml. The resulting solution was stirred at room temperature to precipitate crystals. After standting at room temperature overnight, the crystals were collected by filtration and washed with 3 ml of water resulting in 154 mg of (2R,4R)-monatin/(R)-(−)-2-phenylglycinol salt (0.359 mmole, optical purity 99.9%) in 74.0% yield (to (2R,4R)-monatin).

Example 4

Optical Resolution of the (2R,4R)-isomer and (2S,4R)-isomer of Monatin and Preparation of (2R,4R)-monatin/R-(−)-2-phenylglycinol Salt (Run 4)

A 52:48 mixture of (2R,4R)- and (2S,4R)-isomers of monatin sodium salt (300 mg; 0.952 mmole) and 131 mg (0.952 mmole) of (R)-(−)-2-phenylglycinol were dissolved in 30 ml of water, and the mixture was concentrated under reduced pressure to 3 ml. The resulting solution was stirred at room temperature to precipitate crystals. After standting at room temperature overnight, the crystals were collected by filtration and washed with 3 ml of water resulting in 135 mg of (2R,4R)-monatin/(R)-(−)-2-phenylglycinol salt (0.314 mmole, optical purity 85.0%) in 66.0% yield (to (2R,4R)-monatin).

Example 5

Conversion of (2R,4R)-monatin/(R)-(−)-2-phenylglycinol salt into (2R,4R)-monatin Ammonium Salt (2R,4R)-Monatin/(R)-(−)-2-phenylglycinol salt (275 mg; 0.640 mmole) was dissolved in 20 ml of 5% ammonia water and extracted with 30 ml of toluene 3 times. The aqueous layer was further extracted with 30 ml of ethyl acetate 3 times, and concentrated under reduced pressure, to which was then added 40 ml of ethanol. The precipitated crystals were collected by filtration resulting in 100 mg of (2R,4R)-monatin ammonium salt (0.323 mmole) in 50.5% yield.

Example 6

Optical Resolution of the (2R,4S)-isomer and (2S,4R)-isomer of Monatin and Preparation of (2R,4S)-monatin/R-(−)-2-phenylglycinol salt A 1:1 mixture of (2R,4S)- and (2S,4R)-isomers of monatin ammonium salt (3.00 g; 9.70 mmole) and 1.33 g (9.70 mmole) of (R)-(−)-2-phenylglycinol were dissolved in 50 ml of water, and the mixture was concentrated under reduced pressure to 5 ml. The mixture was stirred at room temperature to precipitate crystals, to which was added 50 ml of isopropanol, and the crystals were collected by filtration. The crystals were redissolved in 50 ml of water, which was concentrated to 5 ml to precipitate crystals. The crystals were collected by filtration and washed with 5 ml of water resulting in 0.937 g of (2R,4S)-monatin phenylglycinol salt (2.18 mmole, optical purity 99.9%) in 44.9% yield (to (2R,4S)-monatin).

NMR (400 MHz, D$_2$O) δ:2.09-2.16 (m, 1H), 2.36-2.41 (m, 1H), 3.14 (s, 2H), 3.65-3.76 (m, 2H), 3.86-3.90 (m, 1H), 4.06-4.09 (m, 1H), 7.05-7.10 (m, 1H), 7.13-7.17 (m, 2H), 7.32-7.42 (m, 6H), 7.65-7.67 (m, 1H). M.p. 96.8-105.3° C.

Example 7

Conversion of (2R,4S)-monatin/(R)-(−)-2-phenylglycinol Salt into (2R,4S)-monatin Sodium Salt (2R,4S)-Monatin/(R)-(−)-2-phenylglycinol salt (215 mg; 0.50 mmole) was dissolved in 20 ml of 5% ammonia water and extracted with 30 ml of ethyl acetate 7 times. The aqueous layer was concentrated under reduced pressure, to which was then added 40 ml of ethanol. The precipitated crystals were collected by filtration resulting in 121 mg of (2R,4S)-monatin sodium salt (0.38 mmole) in 76.0% yield.

Example 8

Optical Resolution of a Mixture of 4 Stereoisomers of Monatin

A mixture of 4 stereoisomers ((2R,4R):(2S,4S):(2R,4S):(2S,4R)=3:3:2:2) of monatin ammonium salt (600 mg; 1.94 mmole) and 160 mg (1.16 mmole) of (R)-(−)-phenylglycinol were dissolved in 30 ml of water, and concentrated under reduced pressure to 5 ml. The resulting solution was stirred at room temperature to precipitate crystals, which were collected by filtration and washed with 5 ml of water. The mother liquor and the washing solution were concentrated to 5 ml and stirred for about 1 hour to give the 2nd crop of crystals. These crystals were redissolved in 50 ml of water, which was then concentrated under reduced pressure to 10 ml. The precipitated crystals were collected by filtration resulting in 178.8 mg of a 9:1 mixture of (2R,4R)-monatin and (2R,4S)-monatin.

Example 9

Optical Resolution of the (2R,4R)-isomer and (2S,4S)-isomer of Monatin and Preparation of (2R,4R)-monatin L-valinol Salt A 1:1 mixture of (2R,4R)- and (2S,4S)-isomers of monatin ammonium salt (600 mg; 1.94 mmole) and 200 mg (1.94 mmole) of (S)-(+)-2-amino-3-methyl-1-butanol were dissolved in 50 ml of water, and the mixture was concentrated under reduced pressure to 2 ml, to which 60 ml of isopropanol was added dropwise. The precipitated crystals were collected by filtration and redissolved in 20 ml of water. The solution was concentrated under reduced pressure to 2 ml, to which 50 ml of isopropanol was added to give crystals, which were collected by filtration resulting in 310 mg of (2R,4R)-monatin L-valinol salt 0.6 isopropanol solvate (0.718 mmole; optical purity 99.9%) in 74.0% yield.

NMR (400 MHz, D$_2$O) δ: 0.91-0.95 (m, 6H), [1.08-1.10 (d, 3.6H)], 1.85-1.91 (m, 1H), 1.94-2.02 (m, 1H), 2.57-2.61 (m, 1H), 2.99-3.04 (m, 2H), 3.19-3.24 (m, 1H), 3.54-3.62 (m, 2H), 3.77-3.81 (m, 1H), [3.92-3.96 (m, 0.6H)], 7.05-7.10 (m, 1H), 7.13-7.17 (m, 2H), 7.40-7.43 (m, 1H), 7.64-7.67 (m, 1H); the numerical values in the square bracket [ ] indicate signals of isopropanol. M.p. 114.5-122.7° C.

Example 10

Conversion of (2R,4R)-monatin L-valinol Salt into (2R,4R)-monatin Ammonium Salt (2R,4R)-Monatin L-valinol salt (1.2 isopropanol solvate) (2.00 g; 4.28 mmole) was dissolved in 100 ml of water, and the mixture concentrated under reduced pressure. This operation for concentration was repeated twice to remove isopropanol contained therein. The residue was dissolved in 50 ml of water, which was slightly acidified with addition of an ion-exchange resin (AMBERLITE IR120B H AG), and the mixture was stirred. The reaction mixture was neutralized with 5% ammonia water. The ion-exchange resin was removed by filtration and washed with 5% ammonia water. The resulting solutions were combined and concentrated under reduced pressure, followed by addition of 50 ml of ethanol to give crystals. The crystals were collected by filtration, redissolved in 5% ammonia water, and the solution was concentrated under reduced pressure, followed by addition of ethanol to give crystals, whereby 492 mg (1.59 mmole) of (2R,4R)-monatin ammonium salt was obtained in 37.1% yield.

Example 11

Conversion of (2R,4R)-monatin L-valinol Salt into (2R,4R)-monatin Sodium Salt (2R,4R)-Monatin L-valinol salt (0.6 isopropanol solvate) (3.78 g; 8.97 mmole) and 4.49 ml (8.97 mmole) of 2N sodium hydroxide aqueous solution were dissolved in 70 ml of water, and the mixture concentrated under reduced pressure 5 ml, to which 200 ml of ethanol was then added to give crystals. The resulting crystals were redissolved in 100 ml of water, and the solution was concentrated under reduced pressure to 5 ml. Addition of 200 ml of ethanol gave 2.60 g (7.69 mmole) of (2R,4R)-monatin Na salt 0.5 ethanol solvate in 85.7% yield.

Example 12

Optical Resolution of the (2R,4R)-isomer and (2S,4S)-isomer of Monatin and Preparation of (2R,4R)-monatin/(S)-(+)-isoleucinol Salt A 1:1 mixture of (2R,4R)- and (2S,4S)-isomers of monatin ammonium salt (300 mg; 0.970 mmole) and 113 mg (0.970 mmole) of (S)-(+)-isoleucinol were dissolved in 30 ml of water, and the mixture was concentrated under reduced pressure to 1 ml. The resulting solution was stirred for a while to precipitate crystals, which were collected by filtration and washed with 50% ethanol aqueous solution to give 28.3 mg of (2R,4R)-monatin (S)-(+)-isoleucinol salt (0.069 mmole; optical purity 99.9%) in 7.1% yield. The mother liquor was concentrated under reduced pressure, and the residue was dissolved in 10 ml of water. The solution was subsequently concentrated under reduced pressure to 5 ml. To the resulting reaction mixture 50 ml of 1:1 mixture of ethanol and isopropanol was dropwise added with stirring to precipitate crystals, which were collected by filtration to give 83.4 mg of (2R,4R)-monatin (S)-(+)-isoleucinol salt as a 2nd crop (0.204 mmole; optical purity 69%) in 21.0% yield.

Example 13

Conversion of (2R,4R)-monatin Sodium Salt into (2R,4R)-monatin Ammonium Salt (2R,4R)-Monatin sodium salt 0.1 ethanol solvate (640 mg; 2.00 mmole) was dissolved in 20 ml of water, and the mixture concentrated under reduced pressure. Concentration was repeated twice to remove ethanol. The residue was dissolved in 4 ml of water, to which 2 ml (2.00 mmole) of IN hydrochloric acid aqueous solution was then dropwise added with stirring to precipitate crystals. After stirring the solution for 20 minutes, the crystals were collected by filtration and washed with 3 ml of cold water. The crystals were further washed as slurry in 4 ml of cold water and collected by filtration. The crystals were dissolved in 5% ammonia water, and the solution was concentrated under reduced pressure. The residue was crystallized from 30 ml of ethanol resulting in 502 mg (1.62 mmole) of (2R,4R)-monatin ammonium salt in 81.0% yield.

Example 14

Conversion of (2R,4R)-monatin Ammonium Salt into (2R,4R)-monatin L-valinol Salt (2R,4R)-Monatin ammonium salt (473 mg; 1.53 mmol) and 158 mg (1.53 mmole) of (S)-(+)-2-amino-3-methyl-1-butanol were dissolved in 10 ml of water, and the solution was concentrated under reduced pressure. The residue was crystallized from 30 ml of isopropanol resulting in 540 mg (1.37 mmole) of (2R,4R)-monatin L-valinol salt in 101% yield.
NMR (400 MHz, $D_2O$) δ: 0.91-0.96 (m, 6H), 1.86-1.92 (m, 1H), 1.95-2.02 (m, 1H), 2.58-2.62 (m, 1H), 3.00-3.05 (m, 2H), 3.20-3.24 (m, 1H), 3.54-3.63 (m, 2H), 3.77-3.82 (m, 1H), 7.06-7.10 (m, 1H), 7.13-7.17 (m, 2H), 7.41-7.43 (m, 1H), 7.64-7.67 (m, 1H). M.p. 168.4-170.9° C.

Example 15

Conversion of (2R,4R)-monatin Ammonium Salt into (2R,4R)-monatin Arginine Salt (2R,4R)-Monatin ammonium salt (472 mg; 1.53 mmole) and 267 mg (1.53 mmole) of L-arginine were dissolved in 20 ml of water, and the solution was concentrated under reduced pressure. 30 ml of isopropanol was added to the residue resulting in crystals, and the slurry was stirred for 30 minutes. The crystals were collected by filtration resulting in 660 mg (1.28 mmole) of (2R,4R)-monatin L-arginine salt 0.8 isopropanol solvate in 83.7% yield.
NMR (400 MHz, $D_2O$) δ: [1.08-1.10 (m, 4.8H)], 1.54-1.66 (m, 2H), 1.76-1.80 (m, 2H), 1.94-2.02 (m, 1H), 2.57-2.62 (m, 1H), 2.99-3.03 (m, 1H), 3.10-3.14 (m, 2H), 3.19-3.23 (m, 1H), 3.54-3.58 (m, 1H), 3.62-3.65 (m, 1H), [3.90-3.97 (m, 0.8H)], 7.05-7.09 (m, 1H), 7.13-7.17 (m, 2H), 7.40-7.43 (m, 1H), 7.64-7.66 (m, 1H); the numerical values in the square bracket [ ] indicate signals of isopropanol. M.p. 129.3-141.5° C.

Example 16

Conversion of (2R,4R)-monatin Ammonium Salt into (2R,4R)-monatin Lysine Salt (2R,4R)-Monatin ammonium salt (502 mg; 1.62 mmol) and 237 mg (1.62 mmole) of L-lysine were dissolved in 10 ml of water, and the solution was concentrated under reduced pressure. 20 ml of ethanol was added to the residue resulting in crystals, whereby 643 mg (1.39 mmole) of (2R,4R)-monatin lysine salt 0.5 ethanol solvate was obtained in 85.8% yield.
NMR (400 MHz, $D_2O$) δ:[1.08-1.12 (m, 1.5H)], 1.30-1.47 (m, 2H), 1.59-1.66 (m, 2H), 1.78-185 (m, 2H), 1.95-2.01 (m, 1H), 2.57-2.62 (m, 1H), 2.91-2.95 (m, 2H), 2.99-3.04 (m, 1H), 3.19-3.23 (m, 1H), [3.54-3.55 (m, 0.5H)], 3.56-3.60 (m, 1H), 3.64-3.68 (m, 1H), 7.05-7.10 (m, 1H), 7.13-7.17 (m, 2H), 7.40-7.43 (m, 1H), 7.64-7.67 (m, 1H); the numerical values in the square bracket [ ] indicate signals of ethanol. M.p. 168.4-170.9° C.

Example 17

Conversion of (2R,4R)-monatin Valinol Salt into (2R,4R)-monatin Calcium Salt (2R,4R)-Monatin valinol salt 1.2 isopropanol solvate (500 mg; 1.07 mmole) and 79.3 mg (1.07 mmole) of calcium hydroxide were dissolved in 200 ml of water, and the solution was concentrated under reduced pressure to 3 ml. Addition of 50 ml of ethanol resulted in crystal precipitation. The crystals were collected by filtration and redissolved in 200 ml of water. The solution was subsequently concentrated under reduced pressure. Ethanol was added to the residue to give crystals, and the crystals were collected by filtration. 3 ml of water was added to the crystals, and the slurry was concentrated under reduced pressure to remove water and ethanol contained, resulting in 294 mg (0.885 mmole) of (2R,4R)-monatin calcium salt in 82.7% yield.

M.p. 229.8-243.3° C.

Example 18

Conversion of (2R,4R)-monatin Valinol Salt into (2R,4R)-monatin Potassium Salt (2R,4R)-Monatin valinol salt 1.2 isopropanol solvate (500 mg; 1.07 mmole) and 90 mg (1.36 mmole) of potassium hydroxide (85% purity) were dissolved in 50 ml of water, and the solution was concentrated under reduced pressure. 50 ml of ethanol was added to the residue to give crystals, whereby 262 mg (0.792 mmole) of (2R,4R)-monatin potassium salt was obtained in 73.9% yield.

Example 19

Conversion of (2R,4R)-monatin Sodium Salt into Mixed Crystals (Salt) of (2R,4R)-monatin and Aspartame (Run 1)

(Monatin RR/Asparame HCl 1.0 equivalent)

To 1 ml of water 160 mg (0.5 mmole) of (2R,4R)-monatin sodium salt 0.1 ethanol solvate and 147 mg (0.5 mmole) of aspartame was added, and the resulting slurry was heated at 50° C. 1N Hydrochloric acid aqueous solution (0.5 ml; 1.0 equivalent) was added dropwise thereto over 20 minutes, and after completion of the addition the mixture was stirred for 10 minutes. The mixture was then cooled at 0° C. for 30 minutes, and the crystals were collected by filtration resulting in 221 mg of (2R,4R)-monatin aspartame mixed crystals (salt) [(2R,4R)-monatin:aspartame=1:0.7 (molar ratio); 0.435 mmole] in 87.2% yield.

Example 20

Conversion of (2R,4R)-monatin Sodium Salt into Mixed Crystals (Salt) of (2R,4R)-monatin and Aspartame (Run 2)

In the same manner as in Example 19, except for use of 0.45 ml (0.9 equivalent) of 1N hydrochloric acid aqueous solution, 235 mg of (2R,4R)-monatin aspartame mixed crystals (salt) [(2R,4R)-monatin:aspartame=1:0.8 (molar ratio); 0.448 mmole] was prepared in 89.4% yield.

Example 21

Conversion of (2R,4R)-monatin Sodium Salt into Mixed Crystals (Salt) of (2R,4R)-monatin and Aspartame (Run 3)

In the same manner as in Example 19, except for use of 0.55 ml (1.1 equivalent) of 1N hydrochloric acid aqueous solution, 187 mg of (2R,4R)-monatin aspartame mixed crystals (salt) [(2R,4R)-monatin:aspartame=1:0.6 (molar ratio); 0.396 mmole] was prepared in 79.3% yield.

Example 22

Conversion of (2R,4R)-monatin Sodium Salt into Mixed Crystals (Salt) of (2R,4R)-monatin and Aspartame (Run 4)

In 200 ml of water was dissolved 0.85 g (2.70 mmole) of (2R,4R)-monatin sodium salt 0.1 ethanol solvate and 0.87 g (2.97 mmole) of aspartame, and the solution was adjusted at pH 4.44 with 1N hydrochloric acid. The solution was concentrated under reduced pressure to 50 ml to precipitate crystals. The crystals were heated at 50° C. as slurry for 1 hour and collected by filtration to give 0.985 g of (2R,4R)-monatin aspartame mixed crystals (salt) [(2R,4R)-monatin:aspartame=100:105 (molar ratio); 1.64 mmole] was prepared in 60.7% yield.

NMR (400 MHz, $D_2O$) δ:2.00-2.06 (m, 1H), 2.61-2.78 (m, 3H), 2.97-3.08 (m, 2H), 3.16-3.28 (m, 2H), 3.59-3.63 (m, 1H), 3.67 (s, 3H), 4.11-4.14 (m, 1H), 7.06-7.10 (m, 1H), 7.13-7.33 (m, 7H), 7.41-7.43 (m, 1H), 7.63-7.66 (m, 1H).

M.p. 157.7-159.2° C.

Numerous modifications and variations on the present invention are possible in light of the above teachings. It is, therefore, to be understood that within the scope of the accompanying claims, the invention may be practiced otherwise than as specifically described herein.

The invention claimed is:

1. A crystal form of an organic amine salt of (2R,4R)-monatin, wherein said organic amine is (R)-(−)-2-phenylglycinol, and which has PXRD peaks at diffraction angles 2θ±0.2° of 5.3°, 17.4°, 18.5°, 19.0° and 21.2°.

2. The crystal form as claimed in claim 1, wherein said organic amine salt has a chemical purity of at least 95%.

3. The crystal form as claimed in claim 1, wherein said organic amine salt has an optical purity of at least 95%.

4. A crystal form of an organic amine salt of (2R,4R)-monatin, wherein said organic amine is L-valinol, and which has PXRD peaks at diffraction angles 2θ±0.2° of 5.7°, 9.0°, 17.3°, 19.8° and 20.8°.

5. The crystal form as claimed in claim 4, wherein said organic amine salt has a chemical purity of at least 95%.

6. The crystal form as claimed in claim 4, wherein said organic amine salt has an optical purity of at least 95%.

7. The crystal form as claimed in claim 1, which has PXRD peaks at diffraction angles 2θ±0.2° of 5.3°, 17.4°, 17.7°, 18.5°, 19.0° and 21.2°.

8. The crystal form as claimed in claim 1, which has PXRD peaks at diffraction angles 2θ±0.2° of 5.3°, 15.2°, 17.4°, 17.7°, 18.5°, 19.0° and 21.2°.

9. The crystal form as claimed in claim 4, which has PXRD peaks at diffraction angles 2θ±0.2° of 5.7°, 9.0°, 17.3°, 19.8°, 20.1° and 20.8°.

10. The crystal form as claimed in claim 4, which has PXRD peaks at diffraction angles 2θ0.2° of 5.7°, 9.0°, 14.9°, 17.3°, 19.8°, 20.1° and 20.8°.

11. A crystal form of an organic amine salt of (2R,4S)-monatin, wherein said organic amine is (R)-(−)-2-phenylglycinol, and which has PXRD peaks at diffraction angles 2θ±0.2° of 5.6°, 18.1°, 18.5°, 19.1° and 22.3°.

12. The crystal form as claimed in claim 11, wherein said organic amine salt has a chemical purity of at least 95%.

13. The crystal form as claimed in claim 11, wherein said organic amine salt has an optical purity of at least 95%.

14. The crystal form as claimed in claim 11, which has PXRD peaks at diffraction angles 2θ±0.2° of 5.6°, 15.1°, 18.1°, 18.5°, 19.1° and 22.3°.

15. The crystal form as claimed in claim 11, which has PXRD peaks at diffraction angles 2θ±0.2° of 5.6°, 7.5°, 15.1°, 18.1°, 18.5°, 19.1° and 22.3°.

16. A crystal form of an organic amine salt of (2R,4R)-monatin, wherein said organic amine is aspartame, and which has PXRD peaks at diffraction angles 2θ±0.2° of 17.9°, 19.2°, 21.3°, 23.9° and 27.8°.

17. The crystal form as claimed in claim 16, which has PXRD peaks at diffraction angles 2θ±0.2° of 11.9°, 17.9°, 19.2°, 21.3°, 23.9° and 27.8°.

18. The crystal form as claimed in claim 16, which has PXRD peaks at diffraction angles 2θ±0.2° of 6.0°, 11.9°, 17.9°, 19.2°, 21.3°, 23.9° and 27.8°.

19. The crystal form as claimed in claim 16, wherein said organic amine salt has a chemical purity of at least 95%.

20. The crystal form as claimed in claim 16, wherein said organic amine salt has an optical purity of at least 95%.

* * * * *